United States Patent [19]

Koch et al.

[11] Patent Number: 5,436,459
[45] Date of Patent: Jul. 25, 1995

[54] UV SPECTROMETER WITH LASER DIODES AND LASER FREQUENCY MULTIPLICATION

[75] Inventors: Edmund Koch; Ulrich Heim, both of Lübeck, Germany

[73] Assignee: Drägerwerk Aktiengesellschaft, Lubeck, Germany

[21] Appl. No.: 191,634

[22] Filed: Feb. 4, 1994

[30] Foreign Application Priority Data

Mar. 10, 1993 [DE] Germany .................. 43 07 595.9

[51] Int. Cl.[6] ............................................. G01N 21/31
[52] U.S. Cl. ................................... 250/373; 250/375
[58] Field of Search .............. 250/373, 375, 339, 340, 250/341; 356/51, 320; 359/328, 326

[56] References Cited

U.S. PATENT DOCUMENTS

| | | |
|---|---|---|
| 4,450,356 | 5/1984 | Murray et al. |
| 5,142,542 | 8/1992 | Dixon .................. 359/326 |
| 5,317,447 | 5/1994 | Baird et al. .......... 359/328 |

FOREIGN PATENT DOCUMENTS

4110095A1 10/1992 Germany .

OTHER PUBLICATIONS

Demtröder, Wolfgang Laser Spectroscopy Basic Concepts and Instrumentation Springer Series in Chemical Physics pp. 357–371.
Radziemski, Solarz Laser Spectroscopy and its Applications Lasers for Spectroscopy pp. 139–147.
Andrews, David L. Applied Laser Spectroscopy: Techniques, Instrumentation, and Applications Ultrafast Spectroscopic Methods pp. 402–408.

*Primary Examiner*—Paul M. Dzierzynski
*Assistant Examiner*—Richard Hanig
*Attorney, Agent, or Firm*—McGlew and Tuttle

[57] ABSTRACT

A laser spectrometer suitable for detecting gas components in a test sample in the ultraviolet range. The measuring laser radiation (2) is sent to a nonlinear crystal (20, 40, 41), which increases the nominal laser frequency to the frequency that corresponds to the absorption wavelength of the measured gas. Tripling of the frequency takes place either after passage of the radiation through a single nonlinear crystal (20), or by mixing a frequency-doubled laser beam with the measuring laser radiation (2) in a common, second nonlinear crystal (41).

9 Claims, 3 Drawing Sheets

UV SPECTROMETER WITH LASER DIODES AND LASER FREQUENCY MULTIPLICATION

FIELD OF THE INVENTION

The present invention pertains to a method and device for the spectroscopic measurement of gas components in a measuring chamber, which is irradiated by the measuring radiation of a modulated laser diode, which is connected for this purpose to a temperature and/or current modulation unit for the laser frequency, so that the emission wavelength of the laser radiation is identical to at least one absorption wavelength of the measured gas in the measuring chamber, with a radiation sensor, which receives the measuring radiation exiting after its passage through the measuring chamber.

BACKGROUND OF THE INVENTION

Such a device has become known from German Offenlegungsschrift No. DE-OS 41 10 095. This prior-art spectrometer uses a laser diode as the transmitting unit, which is operated with a modulated control current. The modulated laser radiation penetrates a gas cuvette, in which the transmitted radiation is attenuated, with a corresponding superimposition of the radiation wavelength and the absorption wavelength, in proportion to the amount of gas components to be detected in the measuring chamber. To generate a state of inversion, the laser diode is supplied with a constant current, which is modulated at a frequency in the kHz range. Due to this modulation, the laser frequency or wavelength is tunable within a wavelength range of one tenth to a few nanometers (nm), depending on the design of the laser diode. A radiation detector receives the laser radiation passing through the measuring chamber and generates a measured signal as a function of the absorption of the laser radiation in the measuring chamber. The second or higher derivation of the measured signal (derivative spectroscopy) is usually used for the evaluation. The measured signal received is evaluated by an electronic circuit (lock-in amplifier), and it is displayed. In the case of the prior-art spectrometer, it is the concentration of oxygen in the measuring chamber. The prior-art device operates with a laser diode, whose emission radiation is in the range of the red spectrum (760–770 nm).

Many of the gas components to be investigated in a gas mixture absorb especially readily in a narrow-band wavelength range of the ultraviolet range, but this section is poorly accessible to common laser spectroscopy with simple means.

It has been known (J. R. Murray: *Laser Spectroscopy and its Applications*, New York, 1987) that tunable lasers in the UV range can be obtained by frequency multiplication.

However, the prior art spectrometers require an expensive technique and are expensive because of the high output requirement of the laser beams used, they require much energy, and they are not readily portable.

SUMMARY AND OBJECTS OF THE INVENTION

The principal object of the present invention is to provide a device and method of that will be suitable for the spectroscopy of gas samples in the ultraviolet range, and It is a further object of the invention to provide an inexpensive, and selectively operating measuring instrument of high sensitivity of detection and yet compact in size. The present invention is a spectrometer with lower power consumption, especially in the case of the use of laser diodes as the radiation source, and due to the high sensitivity of detection, reliable evaluation is possible by sufficiently suppressing interfering signals. Advantages of the present invention are essentially the fact that a portable and lightweight spectrometer, equipped with reliable radiation source, is able to utilize even weak light signals of a laser diode for a nearly interfering signal-free evaluation.

These objects are obtained by directing the emission laser radiation to at least one nonlinear crystal, which increases the nominal laser frequency for frequency multiplication to the value which is identical to the absorption wavelength of the measured gas. Prior-art laser diodes, which deliver a radiated power of about 100 mW in the range of 780±10 nm, undergo a frequency doubling or even tripling after passage through a nonlinear crystal, and the input power decreases to about 10 $\mu$W after doubling and further by a factor of $10^{-2}$ or $10^{-3}$ after tripling. A radiation wavelength of 390 and 260 nm, respectively, is correspondingly obtained after passage through the nonlinear crystal. Crystals for frequency doubling or tripling consist of, e.g., KDP ($KH_2PO_4$) or KTP ($KTiPO_4$). The low power obtained by frequency multiplication is nevertheless sufficient for spectroscopy in the ultraviolet range, because detectors which have practically no dark current or noise are available in this spectral range. Such a detector is available, e.g., from the firm of Hamamatsu under the model designation 981, which has a noise power of only $3 \times 10^{-15}$ W/$\sqrt{Hz}$. In a one-second measuring time, a signal-to-noise ratio of $10^4$ remains behind. This means that $10^9$ photons/sec, which is still sufficiently detectable over the noise of the detector, are still detected at a power of, e.g., 1 nW, which is obtained after frequency tripling. If, moreover, the laser diode operates only in the pulsed mode, higher output powers are also possible, even after frequency tripling or quadrupling.

The wavelength can be changed by varying the temperature of, or the current through, the semiconductor laser. The temperature is usually used for the approximate adjustment of the wavelength of a semiconductor laser, and the current is used for fine modulation. A current that is constant during the pulse (or a constant power) may also be very readily applied in the case of a pulsed laser. In this case, the laser changes its wavelength during the pulse during internal heating, so that the laser frequency is thus varied. The changes in the detector signal over time are detected. The absorption of the gas component to be detected in the sample can be inferred by evaluating the detector signal after passage of the laser through the measuring chamber.

Not only derivative spectroscopy can be considered as the spectroscopic method, but all methods known from laser spectroscopy, e.g., frequency modulation spectroscopy, may be used as well.

The detection of benzene has proved to be a particularly good example of UV spectroscopy in the wavelength range of 240 nm to 270 nm, because pronounced, discrete absorption lines with a half-width value markedly lower than one nm, which are therefore well suited for derivative spectroscopy, are seen in its ultraviolet spectrum. The narrow range for the frequency variation of the semiconductor laser has proved to be advantageous here, and sufficient power is still available in the pulsed mode for detecting a perceptible absorption signal. A laser diode is used for this purpose; the nominal radiation frequency of this laser diode is tripled from about 780 nm by at least one nonlinear crystal, so that the resulting measuring wavelength is 260 nm. By selecting suitable laser diodes and by varying the current or the temperature of the laser diode, the measuring wavelength used can be varied to the extent that it can cover the absorption lines of benzene at the wavelengths of 245, 249, 255, and 260 nm. A simple, lightweight, portable instrument for detecting benzene is thus obtained.

Besides benzene, an interfering gas, with respect to which the measuring detector has a cross sensitivity, is usually also present in the gas sample to be investigated. This interfering gas is mostly toluene. Conventional spectroscopic methods can distinguish the two components, namely, benzene and toluene, only at a considerable measuring technical effort because of their insufficient spectroscopic resolution. However, if the frequency-multiplied emission radiation of a laser diode is used, this cross sensitivity can be easily suppressed. To do so, a reference beam is branched off from the laser emission beam by a beam splitter, and this reference beam is passed through a reference chamber filled with a reference gas. The reference gas may be both the measured gas and the interfering gas. If derivative spectroscopy is used, the selection of the reference gas depends on the relative location of the absorption lines of the measured gas and reference gas to be investigated. The following cases shall be distinguished (the measurement of benzene in the presence of toluene as an interfering gas is used as an example; however, the same procedure can be applied to other gases as well): One of the sharp lines of benzene is clearly separated from a line of the interfering gas, i.e., the lines are not practically overlapped. This benzene line in the absorption spectrum is selected as the measuring wavelength, i.e., the frequency of the laser radiation is increased to the corresponding frequency. Benzene is filled into the reference chamber, and the signal is detected by a reference detector. The third derivation of the reference detector signal is measured through a lock-in amplifier, and is sent as a reference signal to an evaluating unit. This unit stabilizes the laser emission radiation to the zero crossing of the reference signal. The laser radiation is correspondingly attenuated by the maximum absorption occurring at the wavelength in question in the measuring chamber, which also contains benzene. The laser radiation is modulated around this maximum. The signal of the second derivation of the radiation detector is used for the evaluation. (Instead of taking the third derivation in the case of the reference signal, it is also possible to select the first derivation; however, the third derivation offers practical advantages when semiconductor diodes are used.) The measured signal is thus stabilized to the reference signal, and drifts are prevented from occurring. The presence of toluene does not influence the measured signal.

Another procedure is selected when the sharp lines of benzene in any way disturbingly overlap the absorption lines of the interfering gas. The interfering gas is assumed to have a line whose course has a turning or inflection point close to a maximum of the selected line of benzene. The reference chamber is now filled with the interfering gas, and the laser radiation is fixed to the zero crossing of the second derivation of the line of the interfering gas (lock-in amplifier). The measuring radiation is modulated in the vicinity of the absorption maximum, and the signal detected by the radiation detector is used in its second derivation to determine the percentage of benzene. The measured signal is not influenced by the presence of the interfering gas, because its percentage to the evaluated signal is always zero due to the second derivation of the reference signal being fixed to zero. Therefore, if the benzene lines overlap the lines of the interfering gas in any way, a benzene line is selected, at which the maximum or the turning point shows the best possible agreement with a turning point or maximum/minimum, respectively, of the interfering line structure (i.e., the maximum of the benzene line coincides with the turning point of the interfering line, or the turning point of the benzene line coincides with the maximum/minimum of the interfering line as much as possible). Combinations of reference gas fillings and derivations, which completely or extensively suppress the interference signal, are possible in this constellation.

In all devices mentioned above, the measuring chamber is either a closed space, through which the sample is fed (e.g., by means of a pump), or the measuring chamber is an open absorption section, which the sample to be measured enters.

If the emission radiation of the laser is to be tripled, it is desirable to have as much of the available radiation power available after tripling the frequency. Instead of taking a single nonlinear crystal, through which the emission laser radiation penetrates, it is advantageous first to send the emission laser radiation to a first nonlinear crystal to double its frequency, and to subsequently send the frequency-doubled laser radiation, together with the original emission laser radiation, through a second nonlinear crystal. The frequency-doubled radiation is mixed with the original emission laser radiation in the second nonlinear crystal, and it generates third-order harmonic waves of the emission laser radiation. Suitable crystals for frequency doubling and frequency tripling are, besides the KDP and KTP crystals, especially lithium iodate and barium beta-borate.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DETAILED DESCRIPTION OF THE PREFERRED EMBODIMENT

Figure 1:
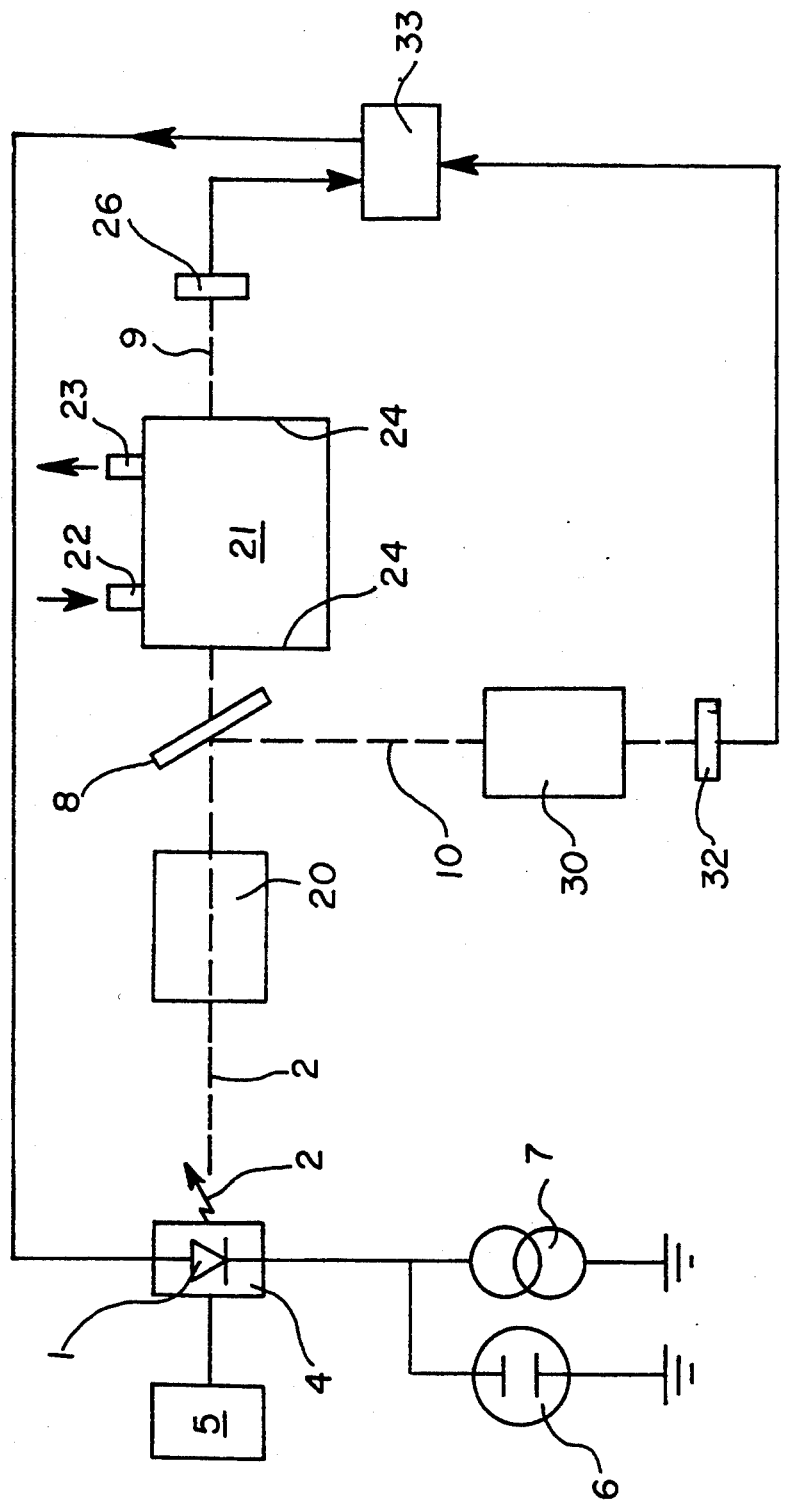
FIG. 1 is a schematic diagram of a UV spectrometer with laser diodes and a nonlinear crystal for frequency doubling.

FIG. 1 shows a laser diode 1, which emits an emission laser radiation 2 of ca. 780 nm. The laser diode 1 is mounted on a temperature stabilizer 4, whose temperature is maintained at a predetermined, constant value by a control unit 5. On the other hand, the control unit 5 can also change the temperature of the temperature stabilizer 4 whereby the laser diode 1 varies the wavelength of its emission laser radiation 2 in a predetermined manner. The laser diode 1 is operated from both a d.c. power source 6 and an a.c. power source 7. The d.c. power source 6 brings about the inversion of the packing density in the laser diode 1, and the a.c. power source 7 brings about the frequency modulation of the emission radiation 2 at constant temperature of the temperature stabilizer 4.

The laser radiation 2 passes through a nonlinear crystal 20. Due to the nonlinear crystal properties of the nonlinear crystal 20 the frequency of the laser radiation is tripled, so that the wavelength of the emission radiation 2 is shortened from the previous value of 780 nm to 260 nm. Behind the crystal 20, the emission radiation 2 passes through a semipermeable beam splitter 8, which splits the emission radiation 2 into a laser radiation portion 9, which is used as the measuring radiation, and a reference radiation portion 10 used for the reference measurement. The laser radiation portion 9 is subsequently passed through a measuring chamber 21, through the inlet 22 and outlet 23 of which a gas sample, which contains benzene and toluene, is fed by a pump element (not shown). The two front surfaces 24 of the measuring chamber 21 facing the laser radiation 9 are permeable to the laser radiation 9, which subsequently falls on a measurement radiation detector 26. The reference radiation portion 10 branched off from the beam splitter 8 passes through a reference chamber 30, which is filled with a reference gas containing a known amount of toluene. The reference radiation 10 is directed toward a reference detector 32. Both the detector signal of the radiation detector 26 and the detector signal of the reference detector 32 are sent to an evaluating and display unit 33. The evaluating and display unit 33 stabilizes the radiation of the laser diode 1 to the zero crossing of the first or second derivation of the reference detector 32.

Figure 2:
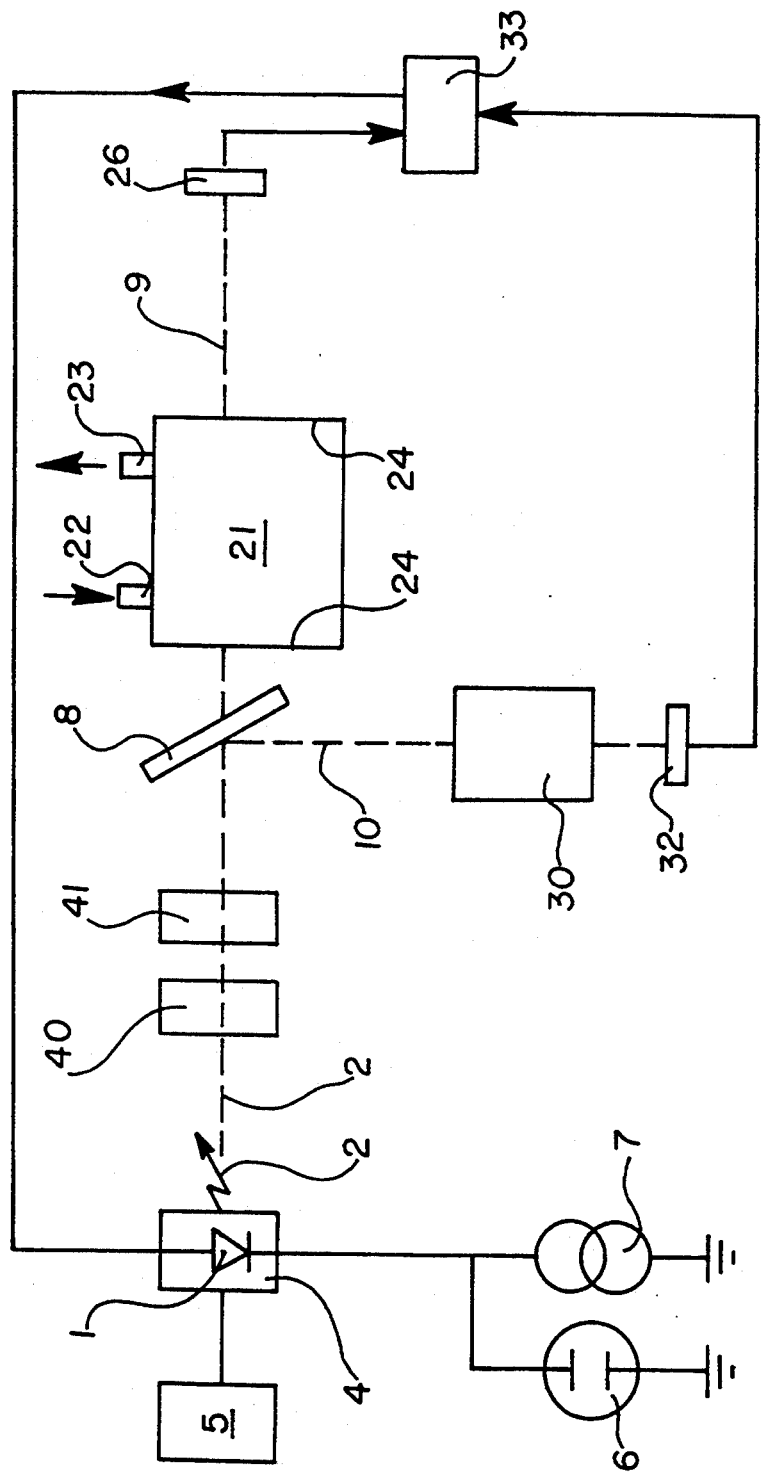
FIG. 2 is a schematic diagram showing a part of the path of rays for the laser radiation for frequency tripling.

FIG. 2 shows the same block diagram as FIG. 1, and identical components are designated by the same reference numerals. The emission laser radiation 2 is passed through two nonlinear crystals 40 and 41 one after the other: After the first crystal 40, frequency-doubled laser radiation of low intensity is emitted, besides the unchanged emission laser radiation 2. Both radiations enter the second nonlinear crystal 41. Third-order harmonic waves, which are formed by a mixture of the fundamental wave of the emission laser radiation 2 and the frequency-doubled laser radiation, are emitted from the second crystal 41. The laser radiation 9, whose frequency has thus been tripled, enters a the measuring chamber 21 and is used for the measurement as explained in FIG. 1.

To preserve the clarity of FIGS. 1 and 2, the means for suppressing the influence of the fundamental wave of the laser emission radiation 2 and of the first harmonic wave on both the radiation detector 26 and the reference detector 32 are not shown. Such means have been known in spectroscopy, and consist of, e.g., dispersive means, such as a filter, prisms, which deflect the interfering wavelength to a screen, by which they are then removed from the path of rays.

It is also favorable to select suitable detectors 26, 32, which are insensitive to the fundamental wavelength and the first harmonic wave, e.g., detectors based on GaAs.

Figure 3:
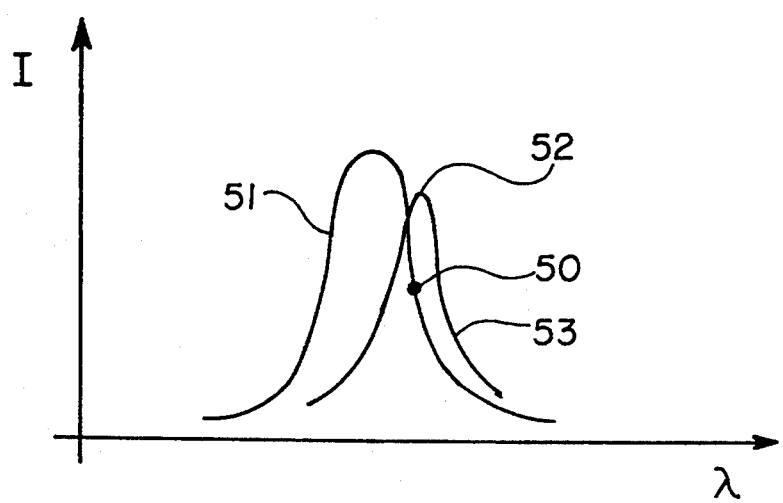
FIGS. 3 and 4 show the location of the measured gas spectral line and the reference gas spectral line in relation to one another.

In FIG. 3, the inflection point 50 of the reference gas spectral line 51 is in the vicinity of the maximum 52 of the measured gas spectral line 53. By forming the second derivative of the reference gas spectral line 51 (the interfering gas spectral line for benzene in the case of the measurement of toluene in the example), this becomes zero at the site of the maximum 52 (zero crossing), and the measured gas spectral line 53 is also formed in its second derivation, and the signal resulting from it is used to determine the percentage of the gas being investigated.

Figure 4:
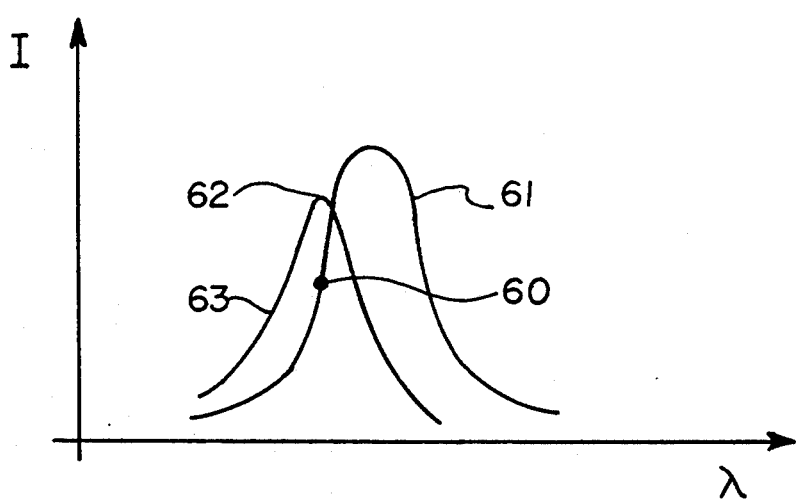

FIG. 4 shows the case in which the inflection point 60 of the measured spectral line 61 coincides with the maximum 62 of the reference gas spectral line 63. To perform the derivative spectroscopy, either the first or the third derivative is formed from both spectral lines 61, 63 and is used for the evaluation.

The wavelength of the laser is tuned such that the maximum or the inflection point of the spectral line of the measured gas will coincide as best as possible with the maximum or minimum of the reference gas spectral line, and the measured signal is obtained by derivative spectroscopy (FIG. 2).

While specific embodiments of the invention have been shown and described in detail to illustrate the application of the principles of the invention, it will be understood that the invention may be embodied otherwise without departing from such principles.

What is claimed is:

1. Device for spectroscopic measurement of gas components, comprising:
   means for defining a measuring chamber for holding gas to be analyzed;
   a modulated laser diode for directing measuring laser radiation through said measuring chamber;
   a temperature and/or current modulation unit connected to said modulated laser diode for changing the wavelength of the measuring laser radiation;
   a radiation detector for receiving measuring radiation exiting after passage through said measuring chamber;
   a nonlinear crystal, said emission laser radiation being directed to said nonlinear crystal for multiplying a nominal frequency of said measuring laser radiation to increase said nominal laser frequency to a frequency which corresponds to an absorption wavelength of the measured gas; and
   a second nonlinear crystal, said measuring laser radiation being sent to said first nonlinear crystal to double its frequency to provide a frequency-doubled laser radiation, said measuring laser radiation and said frequency-doubled laser radiation being sent together to said second nonlinear crystal.

2. A device according to claim 1, wherein:
   said laser diode has a nominal radiation frequency substantially equal to 780 nm, said nonlinear crystal bringing about a tripling of said frequency to increase said frequency to the absorption range of benzene as the measured gas in the wavelength range of 240 nm to 270 nm.

3. A device according to claim 2, wherein:
   said nonlinear crystal is a KDP or ADP crystal (KDP=$KH_2PO_4$; ADP=$NH_4H_2PO_4$).

4. A device according to claim 1, further comprising:
   a beam splitter;
   a reference chamber filled with a reference gas; and
   a reference detector, said beam splitter providing a reference beam, said reference beam being branched off at said splitter and directed through said reference chamber for detection by said reference detector after said reference beam passes through said reference chamber.

5. A device according to claim 2, further comprising:
a beam splitter;
a reference chamber filled with a reference gas; and
a reference detector, said beam splitter providing a reference beam, said reference beam being branched off at said splitter and directed through said reference chamber for detection by said reference detector after said reference beam passes through said reference chamber.

6. A device according to claim 3, further comprising:
a beam splitter;
a reference chamber filled with a reference gas; and
a reference detector, said beam splitter providing a reference beam, said reference beam being branched off at said splitter and directed through said reference chamber for detection by said reference detector after said reference beam passes through said reference chamber.

7. A device according to claim 1, wherein:
said first crystal is a lithium iodate crystal and said second crystal is a barium beta borate crystal.

8. A process for spectroscopic measurement of gas components including an interfering gas and a measure gas, the process comprising:
providing tuneable laser radiation;
passing a first portion of said tuneable laser radiation through the gas components;
recording a measure signal proportional to said first portion of said laser radiation after said first portion has past through the gas components and said first portion has been modulated by the gas components;
recording a reference signal proportional to said second portion of said laser radiation after said second portion has past through the interfering gas and said second portion has been modulated by the interfering gas;
calculating one of a plurality of orders of derivatives of said reference signal, said one derivative of said reference signal having a zero crossing located in an area of one of an inflection point and a maximum point of said measure signal;
adjusting said tuneable laser radiation to said zero crossing of said one derivative of said reference signal;
calculating a derivative of said measure signal, an order of said derivative of said measure signal equalling an order of said one derivative of said reference signal;
calculating a percentage of the measure gas in the gas components from said derivative of said measure signal.

9. A process in accordance with claim 8, wherein:
said reference signal has an inflection point located in an area of said maximum point of said measure signal;
said calculating of said one of said plurality of orders of derivatives of said reference signal and said derivative of said measure signal is performed to a second order.

* * * * *